United States Patent [19]

Utterberg

[11] Patent Number: 5,290,264

[45] Date of Patent: * Mar. 1, 1994

[54] GRIPPABLE GUARD FOR NEEDLE ASSEMBLY

[76] Inventor: David S. Utterberg, 1080 Chestnut St., San Francisco, Calif. 94109

[*] Notice: The portion of the term of this patent subsequent to May 12, 2009 has been disclaimed.

[21] Appl. No.: 753,955

[22] Filed: Sep. 3, 1991

[51] Int. Cl.⁵ ............................................. A61M 5/00
[52] U.S. Cl. ..................................... 604/263; 604/174
[58] Field of Search ............... 604/177, 174, 110, 111, 604/192, 239, 240, 263, 264, 272, 277, 162; 128/919, DIG. 28

[56] References Cited

U.S. PATENT DOCUMENTS

| | | |
|---|---|---|
| 3,323,523 | 6/1967 | Scislowicz et al. |
| 3,463,152 | 8/1969 | Sorenson. |
| 3,568,673 | 3/1971 | Cowley .................. 604/162 |
| 3,572,334 | 3/1971 | Petterson. |
| 4,631,057 | 12/1986 | Mitchell. |
| 4,693,708 | 9/1987 | Wanderer et al. .................. 604/263 |
| 4,832,696 | 5/1989 | Luther et al. ........................ 604/198 |
| 4,840,619 | 6/1989 | Hughes. |
| 4,874,383 | 10/1989 | McNaughton. |
| 4,888,001 | 12/1989 | Schoenberg ........................ 604/162 |
| 4,906,235 | 3/1990 | Roberts ................................ 604/263 |
| 4,917,669 | 4/1990 | Bonaldo ............................... 604/198 |
| 4,935,012 | 6/1990 | Magre et al. |
| 4,941,881 | 7/1990 | Masters et al. ...................... 604/162 |
| 4,950,252 | 8/1990 | Luther et al. ........................ 604/198 |
| 4,985,020 | 1/1991 | Kasuya ................................ 604/263 |
| 5,041,099 | 8/1991 | Gelabert .............................. 604/192 |
| 5,086,780 | 2/1992 | Schmitt ............................... 604/198 |
| 5,112,311 | 5/1992 | Utterberg ............................ 604/177 |
| 5,120,311 | 6/1992 | Sagstetter et al. .................. 604/198 |
| 5,120,320 | 6/1992 | Fayngold ............................. 604/263 |
| 5,171,231 | 12/1992 | Heiliger .............................. 604/192 |

FOREIGN PATENT DOCUMENTS 0425448  5/1991  European Pat. Off. ............ 604/110

*Primary Examiner*—C. Fred Rosenbaum
*Assistant Examiner*—Mark Bockelman
*Attorney, Agent, or Firm*—Gerstman & Ellis, Ltd.

[57] ABSTRACT

A hollow needle carried in a hub, the needle and hub being carried on the end of tubing in flow-communicating relation between the needle and tubing. The hub defines typically a pair of wings extending transversely outwardly from the hub in opposite directions. The wings each carry plate members extending transversely of the wings to facilitate manual gripping of the needle hub. Preferably, the needle and hub further comprises a slidable, tubular guard defining a bore receiving the needle and hub. The tubular guard defines a pair of opposed, longitudinal slots through which the wings extend, with the plate members positioned outside of the tubular guard. The slots permit movement of the needle and hub in the guard from a needle-exposed position to a needle-enclosed position.

12 Claims, 1 Drawing Sheet

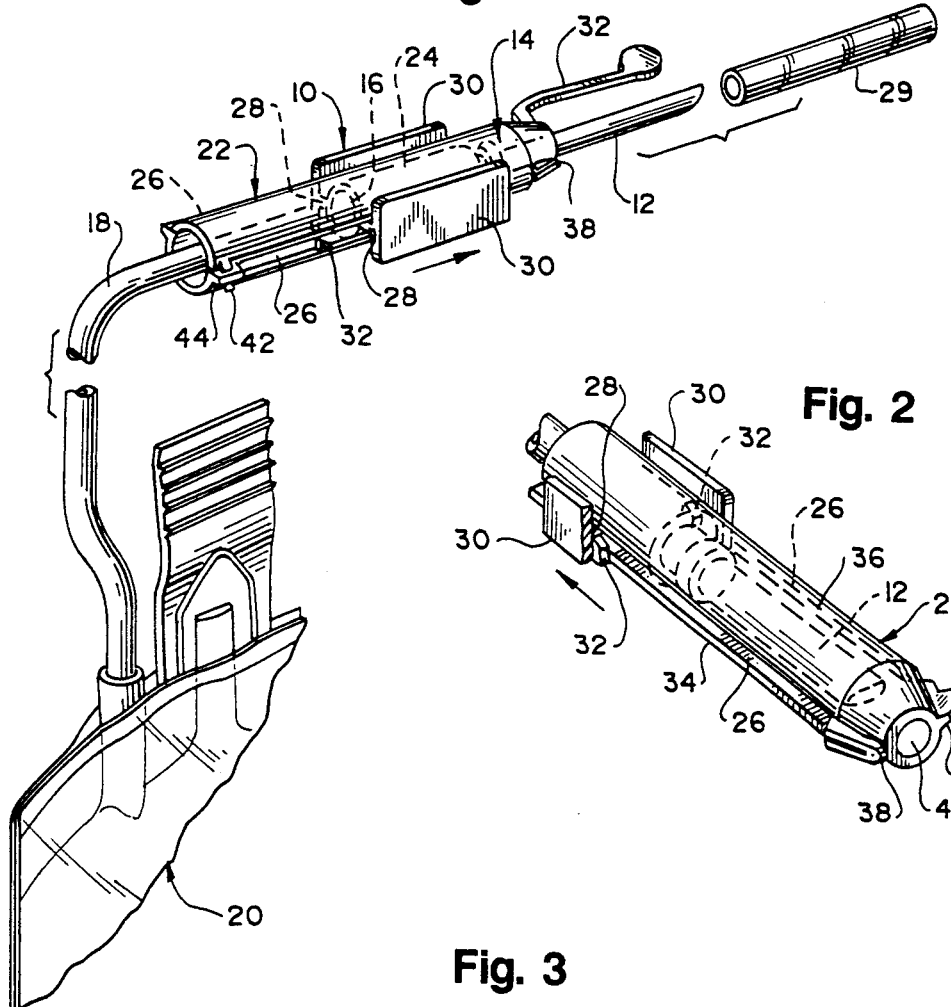

GRIPPABLE GUARD FOR NEEDLE ASSEMBLY

BACKGROUND OF THE INVENTION

As described in the allowed U.S. application Ser. No. 562,419, filed Jul. 30, 1990 by David S. Utterberg, et al. and entitled Guarded Winged Needle Assembly, now U.S. Pat. No. 5,112,311, millions of needles are used on a monthly basis to penetrate the peripheral veins of patients, or to provide to access blood supplies for various extracorporeal treatments such as hemodialysis or plasmapheresis. Many of these assemblies define hubs which carry wings, and, as described in the previously cited application, such a winged hub may carry a slidable, tubular guard defining a bore positioned to receive the needle in the hub. The tubular guard typically defines a pair of opposed, longitudinal slots through which the wings may extend, so that the guard is carried on the needle and hub, and is movable between a needle-exposed position in which the needle may be used to penetrate the vein, and a needle-enclosed position in which the guard surrounds the needle to protect against accidental needle sticks.

Also, millions of needles are used for blood collection, being connected to blood bags by flexible tubing. Here also, there is a need for a protective, slidable, tubular guard to minimize the chances of receiving a needle stick with a needle that has been used to collect blood.

However, it is customary in the field of blood collection for the needle to be carried by a substantially sized hub of generally rectangular cross section. Those who are used to collecting blood with such conventional equipment have become used to the gripping the vertical sides of the enlarged rectangular hub, which gives a particular feel for the manipulation of the blood collection needles, which are relatively larger in gauge and length than conventional IV fluid needles.

By this invention, a system is provided where a slidable, tubular guard can be provided to a needle, but the user can still have the "feel" of a hub which is relatively large and rectangular, even if such a rectangular hub is not present. Thus, the safety of a slidable, tubular guard can be provided, while the "feel" of the needle imparted to the technician who uses the system remains familiar, and the technician also retains the good gripping characteristics with which they are accustomed.

DESCRIPTION OF THE INVENTION

In accordance with this invention, a hollow needle is carried in a hub, the needle and hub being carried on the end of tubing in flow-communicating relation between the needle and the tubing. The hub defines typically a pair of wings, which typically extend transversely outwardly from the hub in opposite directions. The wings each carry plate members, extending transversely of the wings, to facilitate manual gripping of the needle hub. Typically, the plate members are positioned at the exact outer ends of the wings in perpendicular relation thereto, so that the "feel" of the hub as it is gripped is similar to the feel of a hub of rectangular cross section, similar to that conventionally used.

Preferably, the wings and plate members may be made of a substantially rigid or semi-rigid, typically plastic material, and form an integrally molded piece with the rest of the hub, which typically defines a hollow, tubular inner portion that carries the needle at one end and communicates with an end of flexible tubing at the other.

Preferably, the needle and hub assembly of this invention further comprises a slidable, tubular guard defining a bore which is positioned to receive the needle and hub. The tubular guard preferably defines a pair of opposed, longitudinal slots through which the above-described pair of opposed wings extend, with the plate members positioned outside of the tubular guard, although the wings penetrate the slots, and the rest of the hub is inside of the guard. Such longitudinal slots permit movement of the needle and hub in the guard from a needle-exposed position to a needle-enclosed position. Thus, the needle may be used for its conventional medical purpose while occupying relative to the hub a needle-exposed position. Then, when the needle is no longer needed for use, it and the hub may slide relative to the tubular guard into a needle-enclosed position.

Preferably, the tubular guard defines a distal end, having an anchor member which is carried by the distal end and extending forwardly from the distal end. Such an anchor is of a type similar to those shown in the previously cited patent application, capable of being manually held as the needle and hub are withdrawn from penetration of the vein of a patient, to cause sliding of said needle and hub relative to the guard from the needle-exposed position to the needle-enclosed position. Thus, the needle can become protected by being surrounded by the tubular guard simultaneously with the withdrawal of the needle from penetration of the vein of the patient.

It is also preferred for locking means to be provided for holding the needle and hub in the needle-enclosed position once said position is reached, so that the needle and hub do not again move out of the needle-enclosed position.

Preferably, the tubular guard comprises a pair of sections joined along hinge line means, plus means for locking the sections together to define the tubular guard. Thus, the tubular guard may be easily applied to the needle and hub of this invention by being snapped into relation around it. Typically, the tubular guard defines a distal end, with the hinge line means being essentially perpendicular to the axis of the needle, and being defined on the distal end.

DESCRIPTION OF DRAWINGS

In the drawings, FIG. 1 is a perspective view of the hollow needle and hub of this invention, carrying a slidable, tubular guard, with the assembly being carried on the donor tube of a blood bag, and shown in its needle-exposed position;

FIG. 2 is a fragmentary, perspective view of the needle, hub, and tubular guard of FIG. 1, shown in its needle-enclosed position.;

FIG. 3 is a plan view of the needle, hub, and guard, in an intermediate step of the application of the guard to the needle and hub; and FIG. 4 is an elevational view similar to that of FIG. 3.

DESCRIPTION OF SPECIFIC EMBODIMENTS

Referring to the drawings, the apparatus 10 of this invention comprises a hollow intravenous needle 12 carried in a hollow, tubular hub 14 which may be injection molded into adhering relation with needle 12. Hub 14, in turn, is connected in conventional manner at its proximal end 16 to flexible tubing 18, which may connect to a blood or medical solution bag 20, of conventional design.

A hollow, tubular guard 22 is provided, sliding over a generally cylindrical, inner portion 24 of hub 14. Tubular guard 22 defines a pair of opposed, longitudinal slots 26. Hub 14 defines a pair of wings 28 extending transversely outwardly from hub 14 in opposite directions, with each wing 28 respectively extending outwardly through a longitudinal slot 26 of tubular guard 22. Each of wings 28 terminates at its outer end in a plate member 30, which plate member is perpendicular to wings 28. Thus, the two plate members 30 serve as a relatively large available gripping surface for the hub which is easily held and manipulated, and has the "feel" of a rectangular member as normally gripped by the fingers.

Thus, sliding tubular guard 22 can move longitudinally relative to needle 12 and hub 14, with wings 28 of hub 14 being slidable in the respective slots 26 as tubular guard moves proximally or distally relative to needle 12 and hub 14. Specifically, FIG. 1 shows tubular guard 22 in its relatively proximal, needle-exposed position, in which hub 14 may be grasped by the user at plate members 30 to insert needle 12 into the venous system of a patient or elsewhere as desired, after removal of needle cover 29. Then, when needle 12 is to be removed, tubular guard 22 may be moved distally, relative to needle 12 and hub 14, to place the system into the needle-enclosed configuration, as illustrated in FIG. 2, with wings 28 sliding along slot 26 for that purpose.

Specifically, this can be accomplished by means of anchor member 32, which is preferably integrally attached adjacent the forward end of guard 22, extending forwardly therefrom, as shown. Thus, as one withdraws the needle, pressing the skin entry site with a gauze pad, as is conventional. One also presses the anchor member 32 against the skin. This causes tubular guard 22 to remain stationary as needle 12 and hub 14 are withdrawn rearwardly, to bring the system into the needle-enclosed position as needle 12 separates from engagement with the skin, as taught in the previously cited patent application.

As the needle and hub are brought into the needle-enclosed position with tubular guard 22, the respective wings each engage a projection 32, each of which is carried by tubular guard to project into slot 26. Projection 32 defines an angled top surface 33, as shown in FIGS. 1 and 4, so that each wing 28 is impelled to slide over it, as the wing moves rearwardly or proximally relative to guard 22. Then, when each wing 28 has moved completely over its engaged projection 32, it assumes a relationship which is illustrated particularly in FIG. 4, where each wing 26 is blocked by projection 32 so that it is not easy to move wing 26 forwardly again relative to guard 22, so that guard 22 remains locked in the needle-enclosed position. Thus, the freshly used needle may be immediately surrounded with a nonremovable sheath after its use, to protect those who subsequently handle the apparatus.

Tubular guard 22 may comprises a pair of generally semicylindrical sections 34, 36 which are joined together along a divided hinge line 38 having an aperture 40 defined therebetween.

FIGS. 3 and 4 show various aspects of tubular guard 22 in its as-molded configuration. Then, tubular guard 22 may be folded along hinge lines 38 so that the two longitudinally spaced sections are brought together into generally cylindrical shape as shown particularly in FIGS. 1 and 2. A snap lock arrangement is provided comprising tabs 42, which engage with apertures 44 in snap-in locking relationship on each side of one end of guard 22, to lock guard 22 into its folded position in which a tube is defined surrounding needle hub 14. Hub 14 and tubular guard may each be made of a plastic such as polyethylene or polypropylene to provide substantially rigid components with only a relatively small amount of flexibility, although anchor 32 may be provided with a desired amount of flexibility by molding it in thin section. Likewise, hinges 38 are made to be thin enough to provide a desirable plastic hinge.

Thus, a needle and hub is provided which may be manually gripped with ease, with a relatively large transverse gripping surface provided by plates 30. Along with this, slidable, tubular guard is provided so that immediate protection may be provided to needle 12 after use, with the guard 22 being locked in place by the means illustrated after the needle 12 and hub 14 are moved from their needle-exposed position to the needle-enclosed position.

The above has been offered for illustrative purposes only, and is not intended to limit the scope of the invention of this application, which is as defined in the claims below.

That which is claimed is:

1. A hollow needle carried in a hub, said needle and hub being carried on the end of tubing in flow-communicating relation between said needle and tubing, said hub defining a pair of wings extending transversely outwardly from said hub in opposite directions, said wings each carrying plate members extending transversely of said wings, to facilitate manual gripping of said needle hub; a slidable, tubular guard defining a bore positioned to receive said needle and hub, said tubular guard defining a pair of opposed, longitudinal slots through which said wings extend with the plate numbers positioned outside of said tubular guard, said slots permitting movement of said needle and hub in the guard from a needle-exposed position to a needle-enclosed position, said guard defining a distal end; and an elongated anchor member carried by said guard adjacent to and extending distally from said distal end on one side of and spaced from said needle, to be manually held as the needle and hub are withdrawn from penetration of the vein of a patient, to cause sliding of said needle and hub relative to said guard from the needle-exposed to the needle-enclosed position.

2. The needle and hub of claim 1 in which locking means are provided for holding the needle and hub in the needle-enclosed position once said position is reached.

3. The needle and hub of claim 1 in which said tubular guard comprises a pair of sections joined along hinge line means, and means for locking said sections together to define said tubular guard.

4. The needle and hub of claim 3 in which said tubular guard defines a distal end, said hinge line means being essentially perpendicular to the axis of said needle, and being defined on said distal end.

5. A hollow needle carried in a hub, said needle and hub being carried on the end of tubing in flow-communicating relation between said needle and tubing, said hub defining at least one wing carrying a plate member extending transversely of said wing, to facilitate manual gripping of said needle hub; a slidable, tubular guard defining a bore positioned to receive said needle and hub, said tubular guard defining at least one longitudinal slot through which said wing extends with the plate member positioned outside of said tubular guard, said slot permitting movement of said needle and hub in the guard from a needle-exposed position to a needle-enclosed position, said guard defining a distal end; and an elongated anchor member carried by said guard adjacent to and extending distally from said distal end on one side of and spaced from said needle, to be manually held as the needle and hub are withdrawn for penetration of the vein of a patient, to cause sliding of said needle and hub relative to said guard from the needle-exposed to the needle-enclosed position.

6. The needle and hub of claim 5 in which locking means are provided for holding the needle and hub in the needle-enclosed position once said position is reached.

7. The needle and hub of claim 5 in which said wing and plate member are made of a substantially rigid material.

8. A hollow needle carried in a hub, said needle and hub being carried on the end of tubing in flow-communicating relation between said needle and tubing, said hub defining a pair of wings extending transversely outwardly from said hub in opposite directions, said wings each carrying plate members extending transversely of said wings, in which said wings and plate members are made of a substantially rigid material, to facilitate manual gripping of said needle hub, and a slidable, tubular guard defining a bore positioned to receive said needle and hub, said tubular guard defining a pair of opposed, longitudinal slots through which said wings extend with the plate members positioned outside of said tubular guard, said slots permitting movement of said needle and hub in the guard from a needle-exposed position to a needle-enclosed position, said guard defining a distal end; and an elongated anchor member carried by said guard adjacent to and extending distally from said distal end on one side of and spaced from said needle, to be manually held as the needle and hub are withdrawn from penetration of the vein of a patient, to cause sliding of said needle and hub relative to said guard from the needle-exposed o the needle-enclosed position.

9. The needle and hub of claim 8 in which locking means are provided for holding the needle and hub in the needle-enclosed position once said position is reached.

10. The needle and hub of claim 8 which locking means are provided for holding the needle and hub in the needle-enclosed position once said position is reached.

11. The needle and hub of claim 10 in which said tubular guard comprises a pair of sections joined along hinge line means, and means for locking said sections together to define said tubular guard.

12. The needle and hub of claim 11 in which said tubular guard defines a distal end, said hinge line means being essentially perpendicular to the axis of said needle, and being defined on said distal end.

* * * * *